United States Patent
Han et al.

(10) Patent No.: US 6,444,218 B2
(45) Date of Patent: Sep. 3, 2002

(54) SOFT CHEWABLE MULTIVITAMIN TABLET COMPRISING SEPARATED ACTIVE INGREDIENTS

(75) Inventors: Yoon Dong Han, Seoul; Jong Bum Park, Anyang, both of (KR)

(73) Assignee: Sam-A-Pharmaceuticals Co. Ltd., Kyunggi-Do (KR)

( * ) Notice: Subject to any disclaimer, the term of this patent is extended or adjusted under 35 U.S.C. 154(b) by 0 days.

(21) Appl. No.: 09/877,850

(22) Filed: Jun. 8, 2001

Related U.S. Application Data

(62) Division of application No. 09/314,552, filed on May 19, 1999.

(30) Foreign Application Priority Data

Jul. 25, 1998 (KR) .............................. 98-30049

(51) Int. Cl.⁷ .............................. A61K 9/20; A61K 9/24; A61K 31/375; A61K 31/197; A61K 33/24
(52) U.S. Cl. .................. 424/441; 424/439; 424/451; 424/464; 424/465; 424/474; 424/475; 424/476; 424/479; 424/481; 424/600; 424/630; 424/638; 424/641; 424/643; 424/646; 424/647; 424/648; 426/72; 426/73; 426/74; 514/474; 514/563; 514/904; 514/905; 514/960; 514/961; 514/970
(58) Field of Search ................. 514/474, 904, 514/905, 960, 961, 167.168, 563, 970; 424/464, 474, 476, 441, 439, 451, 465, 475, 479, 481, 600, 630, 638, 641, 643, 646–648; 426/72, 74, 73

(56) References Cited

U.S. PATENT DOCUMENTS

| | | | | |
|---|---|---|---|---|
| 3,125,491 A | * | 3/1964 | Elowe et al. ............... | 424/441 |
| 3,247,064 A | * | 4/1966 | Maekawa et al. .......... | 424/471 |
| 3,908,032 A | | 9/1975 | Didelot et al. ............. | 426/660 |
| 4,139,589 A | | 2/1979 | Carrington et al. ........ | 264/250 |
| 4,247,568 A | | 1/1981 | Carrington et al. ........ | 426/321 |
| 4,301,176 A | | 11/1981 | Grabowski et al. ........ | 514/557 |
| 4,327,076 A | | 4/1982 | Puglia et al. ............... | 424/441 |
| 4,450,179 A | | 5/1984 | Vink et al. .................. | 426/103 |
| 4,500,273 A | | 2/1985 | Anderson ................... | 425/123 |
| 4,533,543 A | | 8/1985 | Morris et al. ............... | 424/441 |
| 4,597,981 A | | 7/1986 | Kastin ........................ | 426/660 |
| 4,949,630 A | | 8/1990 | Knebl ....................... | 99/450.7 |
| 5,035,905 A | | 7/1991 | Knebl ........................ | 426/284 |
| 5,567,467 A | | 10/1996 | Kondou et al. ............. | 426/659 |
| 5,578,336 A | | 11/1996 | Monte ......................... | 426/72 |
| 5,626,896 A | | 5/1997 | Moore et al. ............... | 426/103 |
| 5,997,915 A | * | 12/1999 | Bailey et al. ................ | 426/72 |

OTHER PUBLICATIONS

Chemical Abstracts 69:89709h (1968)*

* cited by examiner

*Primary Examiner*—John Pak
(74) *Attorney, Agent, or Firm*—Darby & Darby

(57) ABSTRACT

The present invention provides an improved soft chewable multivitamin tablet in which vitamin C is separated from calcium pantothenate and/or minerals such as iron, copper, zinc and mixtures thereof in a core or multilaminate form and a process for preparing the same. The soft chewable multivitamin tablet of the present invention maintains its stability over a long-storage time in terms of the content and potency of vitamins while overcoming the problems of incompatibility, bad mouthfeel and palatability.

3 Claims, 2 Drawing Sheets

SOFT CHEWABLE MULTIVITAMIN TABLET COMPRISING SEPARATED ACTIVE INGREDIENTS

This application is a divisional of Ser. No. 09/314,552, filed on May 19, 1999.

FIELD OF THE INVENTION

The present invention relates to a soft chewable multivitamin tablet, more specifically, to an improved soft chewable multivitamin tablet in which vitamin C is separated from calcium pantothenate, and/or minerals such as iron, copper, zinc and mixtures thereof in a core or multilaminate form and a process for preparing the same.

BACKGROUND OF THE INVENTION

In general, tablets are prepared by compression of a mixture of active ingredients and pharmaceutically acceptable carriers such as diluting agents. However, the hard nature of conventional tablets does not allow children and the old to take them easily. In this connection, several approaches have been made to prepare tablets having softer mouthfeel in an attempt to overcome said problems and to facilitate easy taking for children and the elderly people.

For example, U.S. Pat. No. 4,327,076 discloses a chewable tablet comprising Premix I (pretreated fat composition containing fatty materials, fat-sorbing materials, tabletting binders, antioxidants, flavors and colorants), Premix II (pretreated active ingredient composition containing antacids, oil binders, emulsifiers, flavors and colorants) and Premix III (pretreated direct compression tabletting aids containing tabletting binders and flavors). However, the prior art chewable tablet has revealed shortcomings as followings: the tablet is uncomfortable to take, because of its bad mouthfeel and palatability; and, an intermediate-type tablet having the characters of hard tablet and soft tablet is produced, since individually prepared Premix I, Premix II and Premix III are simply mixed and tabletted.

Moreover, many multivitamin tablets developed so far are proven to be less satisfactory in the senses that: they have worries of the incompatibility owing to the chemical natures of vitamins or minerals in the tablet containing vitamin complexes, multivitamins-minerals or natural products; and, they revealed undesirable aspects of lowering the content and potency of active ingredients over a long-storage time.

Under the circumstances, there are strong reasons for exploring and developing alternative soft chewable multivitamin tablet which can avoid the chemical interactions among the various vitamins to cause incompatibility while maintaining pleasant mouthfeel and palatable taste.

SUMMARY OF THE INVENTION

The present inventors have made an effort to solve the said problems by partitioning active ingredients whose potencies are affected by the incompatibility, and formulated an improved soft chewable multivitamin tablet in which one component of vitamin C is separated from the other components of calcium pantothenate and/or minerals to maintain a more stabilized pharmaceutical activity over a long-storage time.

A primary object of the present invention is, therefore, to provide a soft chewable multivitamin tablet whose active ingredient of vitamin C is separated from calcium pantothenate, and/or minerals such as iron, copper, zinc and mixtures thereof in a core or multilaminate form.

The other object of the invention is to provide a process for preparing the soft chewable multivitamin tablet which comprises separated active ingredients.

BRIEF DESCRIPTION OF DRAWINGS

The above and the other objects and features of the present invention will become apparent from the following description given in conjunction with the accompanying drawings, in which.

DETAILED DESCRIPTION OF THE INVENTION

Figure 1:
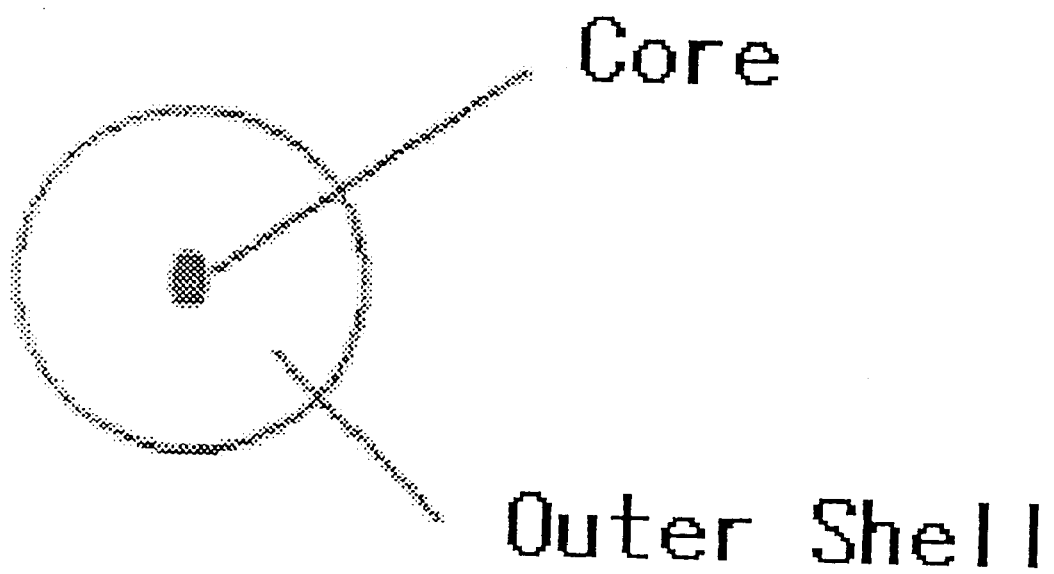
FIG. 1 is a cross-sectional view of a core-type soft chewable multivitamin tablet of the present invention.

A soft chewable multivitamin tablet of the present invention comprises active ingredients, sugars, fatty materials and emulsifiers, wherein an active ingredient of vitamin C is separated from calcium pantothenate, and/or minerals such as iron, copper, zinc and mixtures thereof.

The soft chewable multivitamin tablet of the invention is formulated by a process which comprises the steps of:

(i) dissolving and concentrating sugars in a concentrating tank at a temperature of 120 to 135° C., cooling the concentrated sugars to a temperature of 80 to 100° C., adding a molten mixture of fatty materials and emulsifiers, and kneading to a temperature of 60 to 80° C., adding and thoroughly kneading an active ingredient of vitamin C and the other active ingredients except calcium pantothenate and/or minerals such as iron, copper, zinc and mixtures thereof, or calcium pantothenate and/or the said minerals, and cooling to obtain a kneaded mixture;

(ii) dissolving active ingredients which are different from those contained in the kneaded mixture, together with sugars and a stabilizer at a temperature of 40 to 60° C. to obtain a dispersed material; and, (iii) extruding, rope sizing and tabletting the kneaded mixture and the dispersed material in a separate manner to give a soft chewable multivitamin tablet.

A soft chewable multivitamin tablet of the invention is explained in more detail as below.

A soft chewable multivitamin tablet of the invention comprises active ingredients, sugars, fatty materials and emulsifiers, and may further comprise fondant, gums, flavors, stabilizers and the like to improve mouthfeel and palatability and to stabilize the active ingredients. The active ingredients are contained in a soft chewable multivitamin tablet in an amount of 0.1 to 5 wt %, preferably 0.1 to 25 wt %, which includes vitamins such as vitamin A, vitamin $B_1$, vitamin $B_2$, vitamin $B_6$, vitamin $B_{12}$, vitamin C, vitamin D, vitamin E, vitamin K, nicotinamide, folio acid, calcium pantothenate, biotin and mixtures thereof; mineral supplements such as calcium, calcium carbonate, calcium phosphate, magnesium, magnesium carbonate, magnesium glycerophosphate, manganese, potassium, lecithin, iron, copper, zinc, phosphorus and mixtures thereof; and, herbal rugs such as hippophae rhamnoides ext., pollen, Garcinia, Echinaceae, ginsenoside ext., Ginkgo biloba ext., blueberry, hawthorn ext., acanthopanax ext., aloe ext., Cardus marianus ext. and mixtures thereof.

Further, the soft chewable multivitamin tablet may comprise citric acid or sodium citrate as a stabilizer for vitamin C in a level of 10 to 200 parts, preferably 20 to 80 parts, by weight of the vitamin C 100 parts, whereby vitamin C becomes stabilized to give synergic effect, where the stabilizer plays a dual role as a chelating agent and pH controller as well. In this connection, if the level of stabilizer is lower than the said range, the stabilization cannot be realized, or if it is higher than the said range, the chelation is not realized and pH will rise or fall as well.

In addition, the present invention includes a multivitamin tablet which further comprises sodium citrate for the stabilization of an active ingredient of calcium pantothenate, where calcium pantothenate is stabilized by forming a microenvironment of pH 6 to 7 to permit a long-term storage. Citric acid for stabilizing vitamin C should also be separated from calcium pantothenate.

In the soft chewable multivitamin tablet of present invention, sugars such as white sugar, corn syrup, sorbitol (solution), maltitol (syrup), oligosaccharide, isomaltooligosaccharide, fructose, lactose, glucose, lycasin, xylitol, lactitol, erythritol, mannitol, isomaltose, polydextrose, dextrin and mixtures thereof are added to improve mouthfeel and palatability, in an amount of 50 to 90 wt %, preferably 75 to 85 wt % by weight of the whole tablet.

A soft chewable multivitamin tablet of the invention also comprises fatty materials in an amount of 3 to 15 wt %, preferably 5 to 7 wt %, by weight of the whole tablet, to prevent separation phenomenon and improve mouthfeel. The fatty materials include vegetable oil such as palm oil, palm hydrogenated oil, corn germ hydrogenated oil, castor hydrogenated oil, cotton-seed oil, olive oil, peanut oil, palm olein oil, Cacao fat, margarine, butter, shortening and palm stearin oil, or animal oil such as refined oil and refined lard whose melting point ranges from 30 to 42° C.

To prevent the separation phenomenon and stickiness appearing in the conventional soft chewable tablets and to facilitate conversion of the active ingredients to emulsion or suspension upon taking, the soft chewable multivitamin tablet further comprises emulsifiers such as glycerin fatty acid ester, sorbitan monostearate, sucrose fatty acid ester, lecithin and mixtures thereof, in an amount of 0.01 to 5.0 wt %, preferably 0.05 to 2.0 wt % by weight of the whole tablet. If the level of emulsifier is lower or higher than the said range, the emulsification cannot be realized, or wax value will rise.

To improve the chewiness of the tablet, the soft chewable multivitamin tablet may comprise fondant in an amount of 3 to 20 wt %, preferably 5 to 15 wt %, or gums such as gelatin, agar, arabic gum, guar gum, and carrageenan in an amount of 0.1 to 5 wt %, by weight of the whole tablet. In addition, flavors such as strawberry flavor, tutti fruity flavor, orange flavor, banana flavor and mint flavor may be further included to improve flavorance of the multivitamin tablet.

A process for preparing a soft chewable multivitamin tablet of the present invention is further illustrated as below, where the present inventors separated an active ingredient of vitamin C from the others in a core or multilaminate form, since the contact between one component of vitamin C and the other component of calcium pantothenate, iron, copper, zinc and mixtures thereof, may bring about incompatibility and loss of content and potency of some vitamins.

Preparation of a Soft Chewable Multivitamin Tablet Having a Core

Sugars and water are mixed, dissolved, and concentrated by heating to a temperature of 120 to 135° C. under a reduced pressure of −100 to −500 mmHg in a concentrating tank and cooled to a temperature of 90 to 100° C., where concentration at a high temperature over 135° C. is undesirable because sugars become degraded, conversed, browned or hardened. To the concentrate are added a molten mixture of fatty materials with emulsifier, and kneaded to a temperature 60 to 80° C. and an active ingredient of vitamin C and the other active ingredients except calcium pantothenate and/or minerals such as iron, copper, zinc and mixtures thereof, or calcium pantothenate and/or the said minerals, are added and thoroughly kneaded, and then tempered to a temperature of 40 to 50° C. to obtain a kneaded mixture for outer shell.

On the other hand, sugars, stabilizers and an active ingredient of vitamin C, or the other active ingredients of calcium pantothenate and/or minerals such as iron, copper, zinc and mixtures thereof, which are different from the components contained in the outer shell, are dissolved at a temperature of 40 to 60° C. to obtain a dispersion for core part.

Finally, extruding, rope sizing and tabletting the kneaded mixture for outer shell and the dispersion for core part are carried out to give a soft chewable multivitamin tablet in a core form (see: FIG. 1).

Preparation of a Multilaminated Soft Chewable Multivitamin Tablet

Sugars and water are mixed, dissolved and concentrated by heating to a temperature of 120 to 135° C. under a reduced pressure of −100 to −500 mmHg in a concentrating tank and cooled to a temperature of 90 to 100° C. To the concentrate are added a molten mixture of fat with emulsifier, and kneaded to a temperature of 60 to 80° C., and gums, flavors, stabilizers and an active ingredient of vitamin C and the other active ingredients except calcium pantothenate and/or minerals such as iron, copper, zinc and mixtures thereof, are added and thoroughly kneaded, and then tempered to a temperature of 40 to 50° C. to obtain a kneaded mixture of vitamin C layer.

Then, a kneaded mixture for multivitamins-minerals layer is prepared in a similar manner as in the layer of vitamin C.

Figure 2A:
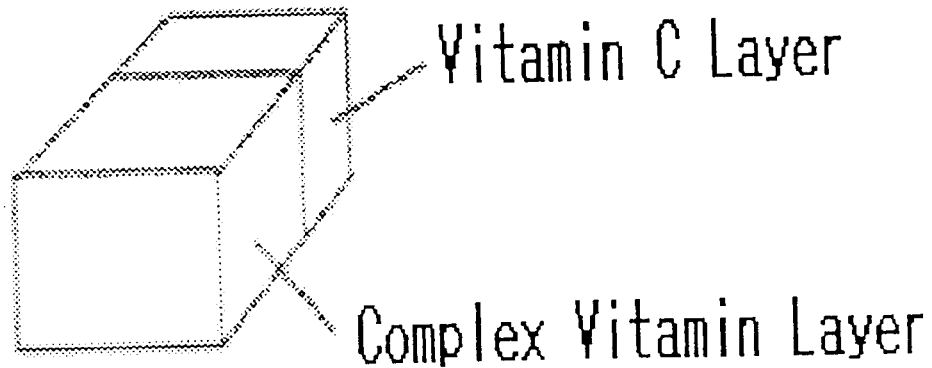
FIG. 2(A) is a perspective view of a double-layered soft chewable multivitamin tablet of the invention.
Figure 2B:
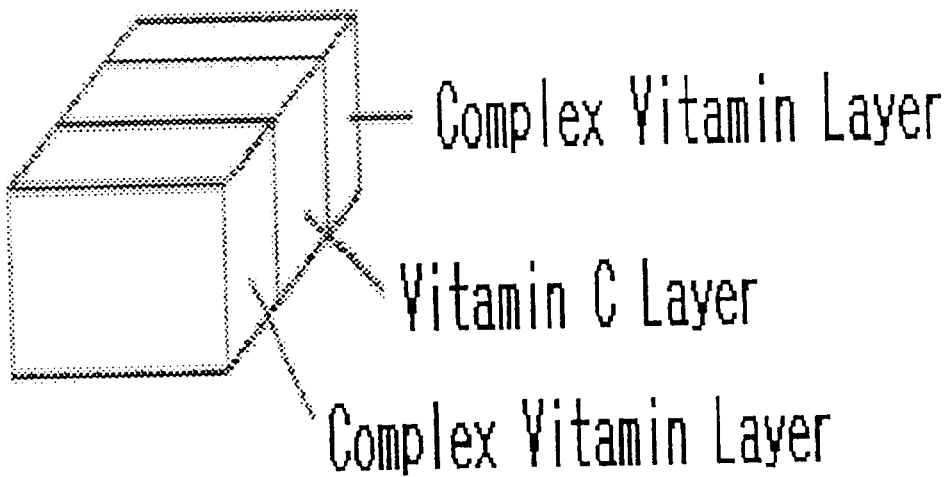
FIG. 2(B) is a perspective view of a three-layered soft chewable multivitamin tablet of the invention.

Finally, the kneaded mixture for vitamin C layer and multivitamins-minerals layer are subjected to an extruder with two inlets (one for the kneaded mixture for the vitamin C layer and the other for the kneaded mixture for the multivitamins-minerals layer), extruded and cooled to give a soft chewable multivitamin tablet in a multilaminate form (see: FIGS. 2A and 2B).

The present invention is further illustrated by the following examples, which should not be taken to limit the scope of the invention.

EXAMPLE 1

A Soft Chewable Multivitamin Tablet Having a Core of Calcium Pantothenate and an Outer Shell Containing Multi-Vitamins White sugar, corn syrup, lactose and water whose contents are shown in Table 1, were mixed, concentrated at 130° C. and then cooled to 90° C. To the concentrated solution were added a molten mixture of hydrogenated vegetable oil with glycerin fatty acid ester and sorbitan monostearate which had been preliminarily prepared, and kneaded to a temperature of 70° C. Then, fondant, gelatin solution, tutti fruity flavor and active ingredients of multi-vitamins whose contents are shown in Table 1, were added to the above mixture, and thoroughly kneaded to a temperature of 40° C. to give a kneaded mixture for outer shell. Subsequently, sodium citrate and calcium pantothenate were added to lycasin in a ratio shown in Table 2, dissolved and then fruit juice powder was added and thoroughly dispersed to give a core dispersion of pH 7. Thereafter, the said kneaded mixture for an outer shell maintained at a temperature of 40° C. was subjected to an extruder equipped with a center filling device, to obtain cylindrical outer shell of a proper width. Then, the core dispersion was pumped into the center of outershell by the aid of centerfilling device. Finally, a core-type soft chewable multivitamin tablet of 4 g was prepared, after extruding, rope sizing and tabletting, and packaged in a sealed form.

TABLE 1

The composition of an outer shell in a soft chewable multivitamin tablet

| Component | | Content |
|---|---|---|
| Sugar | white sugar | 1,140 mg |
| | corn syrup | 1,400 mg |
| | lactose | 175 mg |
| Fatty Material | hydrogenated vegetable | 260 mg |
| Emulsifier | glycerin fatty acid ester | 10 mg |
| | sorbitan monostearate | 3 mg |
| | Fondant | 480 mg |
| Gum | gelatin solution | 14 mg |
| Flavorant | tutti fruity flavor | 6 mg |
| | Water | 130 mg |
| Active Ingredient | vitamin A | 1,000IU |
| | vitamin $B_1$ | 0.65 mg |
| | vitamin $B_2$ | 0.75 mg |
| | vitamin $B_6$ | 0.90 mg |
| | vitamin $B_{12}$ | 0.002 mg |
| | vitamin C (96% granule) | 20.83 mg |
| | vitamin $D_3$ | 115IU |
| | nicotinamide | 5.4 mg |
| | tocopherol acetate | 5.0 mg |
| | folic acid | 0.2 mg |
| | calcium phosphate | 20 mg |
| | magnesium | 10 mg |
| | lecithin | 3.33 mg |
| | hippophae rhamnoides ext. | 6 mg |

TABLE 2

The composition of a core part in a soft chewable multivitamin tablet

| Component | | Content (mg) |
|---|---|---|
| Sugar | lycasin | 450 |
| Stabilizer | sodium citrate | 12 |
| Active Ingredient | calcium pantothenate | 3 |
| | Fruit Juice Powder | 50 |

EXAMPLE 2

A Soft Chewable Multivitamin Tablet Having a Core of Calcium Pantothenate and an Outer Shell Containing Multi-Vitamins and Citric Acid A soft chewable tablet having a core of calcium pantothenate and an outer shell of multi-vitamins and citric acid was prepared in an analogous manner as in Example 1, with an exception of adding 12.5 mg of citric acid to the multi-vatamins component of the outer shell.

EXAMPLE 3

A Soft Chewable Multivitamin Tablet Having a Core of Calcium Pantothenate and an Outer Shell Containing Multi-Vitamins and Citric Acid A soft chewable tablet having a core of calcium pantothenate and an outer shell of multi-vitamins and citric acid was prepared in an analogous manner as in Example 1, with the exceptions of adding 12.5 mg of citric acid to the multi-vitamins component of the outer shell and replacing lycasin with sorbitol solution.

EXAMPLE 4

A Sucrose-Free Soft Chewable Multivitamin Tablet Having a Core of Vitamin C and an Outer Shell Containing Multi-Vitamins corn syrup, lycasin, mannitol, sorbitol solution, lactose and water whose contents are shown in Table 3, were mixed, concentrated at 130° C. and then cooled to 90° C. To the concentrated solution were added a molten mixture of hydrogenated vegetable oil with lecithin and span 60, which had been preliminarily prepared and kneaded to a temperature of 70° C. Then, gelatin solution, strawberry flavor and active ingredients were added to the above mixture, and thoroughly kneaded, and then a kneaded material was prepared to have a material temperature of 40° C. through tempering process. Subsequently, an active ingredient of vitamin C and citric acid, fruit juice powder and tutti fruity flavor were added and thoroughly dispersed to lycasin in accordance with the contents shown in Table 4 to give a homogeneous core dispersion. Thereafter, the said kneaded mixture for an outer shell maintained at a temperature of 40° C. was subjected to an extruder equipped with a center filling device, to obtain cylindrical outer shell of a proper width. Then, the core dispersion was pumped into the center of outershell by the aid of center filling device. Finally, a core-type multivitamin tablet of 4 g was prepared, after extruding, rope sizing and tabletting, and packaged in a sealed form.

TABLE 3

The composition of an outer shell in a soft chewable multivitamin tablet

| Component | | Content (mg) |
|---|---|---|
| Sugar | corn syrup | 1,300 |
| | lycasin | 1,000 |
| | mannitol | 500 |
| | sorbitol solution | 300 |
| | lactose | 150 |
| Fatty Material | hydrogenated vegetable | 260 |
| Emulsifier | lecithin | 5 |
| | Span 60 | 2.5 |
| Gum | gelatin solution | 12 |
| Flavorant | strawberry flavor | 10 |
| | Water | 150 |
| Active Ingredient | vitamin A | 2 |
| | vitamin $B_1$ | 0.65 |
| | vitamin $B_2$ | 0.75 |
| | vitamin $B_6$ | 0.90 |
| | 0.1% vitamin $B_{12}$ | 2 |
| | vitamin $D_3$ | 1.15 |
| | tocopherol | 5 |
| | folic acid | 0.2 |
| | nicotinamide | 5.4 |
| | calcium pantothenate | 3 |
| | calcium phosphate | 20 |
| | magnesium | 10 |
| | lecithin | 3.33 |
| | hippophae rhamnoides ext. | 6 |

TABLE 4

The composition of a core part in a soft chewable multivitamin tablet

| Component | | Content (mg) |
|---|---|---|
| Sugar | lycasin | 430 |
| Stabilizer | citric acid | 15 |
| Flavorant | tutti fruity flavor | 5 |
| Active Ingredient | Vitamin C | 20.83 |
| | Fruit Juice Powder | 30 |

EXAMPLE 5

A Sucrose-Free Soft Chewable Multivitamin Tablet Having a Vitamin C Layer and Multi-Vitamins Layer Corn syrup, maltitol, sorbitol solution, lactose and water whose contents are shown in Table 5, were mixed, concentrated at 130° C. and cooled to 90° C. To the concentrated solution were added a molten mixture of palm hydrogenated oil with lecithin and glycerin fatty acid ester, which had been preliminarily prepared and kneaded to a temperature of 70° C. Then, gelatin solution, strawberry flavor, FD & C Red No. 40, citric acid and an active ingredient of vitamin C whose contents are shown in Table 5 were added to the above mixture, and thoroughly kneaded, and then a kneaded material of vitamin C-containing layer was prepared to have a material temperature of 40° C. through tempering process. Subsequently, corn syrup, maltitol, sorbitol solution, lactose and water were weighed in accordance with the contents shown in Table 5, mixed, concentrated at 130° C. and cooled to 90° C. analogously as in the procedure of vitamin C layer. To the concentrated solution were added a molten mixture of palm hydrogenated oil with lecithin and glycerin fatty acid ester, which had been preliminarily prepared, and kneaded to a temperature of 70° C. Then, active ingredients except for citric acid, strawberry flavor, FD&C Red No. 40 and coated vitamin C were added to the above mixture in accordance with the contents shown in Table 5, and thoroughly kneaded, and then a kneaded material of multi-vitamins layer was prepared to have a material temperature of 40° C. through tempering process. Thereafter, the said kneaded mixtures for vitamin C layer and for multi-vitamins layer maintained at a temperature of 40° C. were subjected to an extruder with two inlets, extruded, cooled, and cut to give a soft chewable multilaminated tablet of 4 g which has vitamin C layer and multi-vitamins layer was prepared, and packaged in a sealed form.

TABLE 5

The composition of a soft chewable multilaminated tablet

| Component | | Vitamin C (mg) | Vitamins (mg) |
|---|---|---|---|
| Sugar | corn syrup | 750 | 750 |
| | maltitol | 500 | 500 |
| | sorbitol solution | 300 | 300 |
| | lactose | 100 | 100 |
| Fatty Material | palm hydrogenated oil | 130 | 130 |
| Emulsifier | lecithin | 2.5 | 2.5 |
| | glycerin fatty acid ester | 5 | 5 |
| Gum | gelatin solution | 6 | 6 |
| Flavorant | strawberry flavor | 5 | — |
| | tutti fruity flavor | — | 6 |

TABLE 5-continued

The composition of a soft chewable multilaminated tablet

| Component | | Vitamin C (mg) | Vitamins (mg) |
|---|---|---|---|
| Colorant | FD&C red No. 40 | 0.25 | — |
| | FD&C yellow No. 203 | — | 0.2 |
| Stabilizer | citric acid | 12.5 | — |
| | Water | 75 | 75 |
| Active Ingredient | vitamin A | — | 2 |
| | vitamin $B_1$ | — | 0.65 |
| | vitamin $B_2$ | — | 0.75 |
| | vitamin $B_6$ | — | 0.9 |
| | 0.1% vitamin $B_{12}$ | — | 2 |
| | vitamin $D_3$ | — | 1.15 |
| | tocopherol acetate | — | 5 |
| | folic acid | — | 0.2 |
| | nicotinamide | — | 5.4 |
| | calcium pantothenate | — | 3 |
| | calcium phosphate | — | 20 |
| | magnesium glycerophosphate | — | 10 |
| | lecithin | — | 3.33 |
| | hippophae rhamnoides ext. | | 6 |
| | vitamin C (type SC) | 20.83 | — |

EXAMPLE 6

A Soft Chewable Multilaminated Tablet Having a Vitamin Layer and Mineral Layer

A multilaminated tablet was prepared in an analogous manner as in Example 5, whose contents are shown in Table 6 below.

TABLE 6

The composition of a soft chewable multilaminated tablet

| Component | | Vitamin (mg) | Mineral (mg) |
|---|---|---|---|
| Sugar | white sugar | 500 | 500 |
| | corn syrup | 700 | 700 |
| | lactose | 100 | 100 |
| | oligosaccharide | 70 | 70 |
| Fatty Material | hydrogenated vegetable | 120 | 120 |
| Emulsifier | lecithin | 2.5 | 2.5 |
| | Span 60 | 2.5 | 2.5 |
| | Fondant | 250 | 250 |
| Gum | arabic gum (50%) | 5 | 5 |
| Stabilizer | citric acid | 20 | — |
| Flavorant | grape flavor | 7.5 | 7.5 |
| | Water | 75 | 75 |
| Active Ingredient | calcium carbonate | — | 187.3 |
| | ferrous fumarate | — | 7.6 |
| | magnesium carbonate | — | 29.6 |
| | vitamin C | 12.5 | — |
| | tocopherol acetate | 7.5 | — |

COMPARATIVE EXAMPLE 1

A Conventional Soft Chewable Tablet Containing Multi-Vitamins

A soft chewable tablet whose components and contents are shown in Table 1 was prepared by mixing all the active ingredients in a simultaneous manner.

White sugar, corn syrup, lactose and water were mixed, concentrated at 130° C. and then cooled to 90° C. To the concentrated solution were added a molten mixture of hydrogenated vegetable oil with glycerin fatty acid ester and sorbitan monostearate, which had been preliminarily prepared and kneaded to a temperature of 70° C. Then, fondant, gelatin solution, tutti fruity flavor and active ingredients were added together with calcium pantothenate in an amount shown in Table 2 to the above mixture, and thoroughly kneaded to a temperature of 40° C. Thereafter, the kneaded mixture maintained at a temperature of 40° C. was subjected to extruding, rope sizing and tabletting to give a soft chewable tablet of 4 g, and packaged in a sealed form.

COMPARATIVE EXAMPLE 2

A Conventional Soft Chewable Tablet Containing Multi-Vitamins and Citric Acid A soft chewable tablet was prepared in an analogous manner as in Comparative Example 1, with an exception of adding 25 mg of citric acid.

COMPARATIVE EXAMPLE 3

A Conventional Soft Chewable Tablet Containing Vitamin and Mineral

A soft chewable tablet was prepared analogously as in Example 6, with an exception of mixing all the active ingredients in a simultaneous manner.

COMPARATIVE EXAMPLE 4

A Conventional Soft Chewable Tablet Having a Core of Calcium Pantothenate Containing Vitamin C and an Outer Shell of Multi-Vitamins A soft chewable tablet having a core was prepared in an analogous manner as in Example 1, with an exception that a core part contains vitamin C which is one of components of the outer shell of Example 1.

COMPARATIVE EXAMPLE 5

A Conventional Soft Chewable Multilaminated Tablet Having a Core of Vitamin C Containing Calcium Pantothenate and an Outer Shell of Multi-Vitamins A soft chewable tablet having a core was prepared in in an analogous manner as in Example 5, with an exception that vitamin C layer contains calcium pantothenate which is one of components of multi-vitamins layer of Example 5.

Stability of Vitamin C and Calcium Pantothenate

The stabilities of vitamin C and calcium pantothenate in the soft chewable tablets prepared in Examples 1 to 6 and Comparative Examples 1 to 5 were examined over a period of 2 years. More than 20 soft chewable tablets were weighed and mean weight per tablet was calculated. Tablets were finely cut and precisely took a weight equivalent to two tablets (40 mg as vitamin C and 6 mg as calcium pantothenate). To this was added 0.1N HCl, dissolved for 30 min, and 0.1N HCl was added again, and dissolved while vortexing. Then, ultrasonication was carried out for 30 min and 100 ml of test solution was prepared by adding 0.1N HCl. On the other hand, vitamin C 1,000 mg and calcium pantothenate 150 mg were dissolved in water to give 50 ml of stock solution. To 2 ml of the stock solution was added 0.1N HCl to obtain 100 ml of standard solution. Thereafter, each of 10 µl of test solution and standard solution was injected to high performance liquid chromatography (HPLC) to give peak area Rt and Rs values respectively, in accordance with the analytical conditions described below and in Table 7. The amounts of vitamin C and calcium pantothenate thus calculated were disclosed in Table 8 below.

Column: Capcellpak $C_{18}$ UG 120(46×250 mm, 5 µm)

Column temperature: 40° C.

Detector: UV spectrophotometer (measured at a wavelength of 210 nm)

Mobile phase:
  A—70% (v/v) acetonitrile
  B—5 mM hexane sodium sulfonate in 20 mM phosphate/acetonitrile (91:9, v/v)
  C—water Calculation:

$$\text{amount of vitamin C}(C_6H_8O_6)\,(\text{mg}) = \text{amount of standard (mg)} \times \frac{Rt}{Rs} \times \frac{1}{25}$$

$$\text{amount of calcium pantothenate }(C_{18}H_{32}CaN_2O_{10})(\text{mg}) = \text{amount of standard (mg)} \times \frac{Rt}{Rs} \times \frac{1}{25}$$

TABLE 7

Flow rate and concentration gradient of mobile phase in HPLC

| Time (min) | Flow Rate (ml/min) | % A | % B | % C |
|---|---|---|---|---|
| 0 | 0.8 | — | 70 | 30 |
| 9 | 0.8 | — | 70 | 30 |
| 9.5 | 0.8 | — | 100 | — |
| 24 | 0.8 | — | 100 | — |
| 24.5 | 0.8 | 8 | 92 | — |
| 36 | 0.8 | 8 | 92 | — |
| 36.5 | 0.8 | — | 70 | 30 |

TABLE 8

Stabilities of vitamin C and calcium pantothenate in soft chewable tablets (%)

| | Examples | | | | | | Comparative Examples | | | | |
|---|---|---|---|---|---|---|---|---|---|---|---|
| | 1 | 2 | 3 | 4 | 5 | 6 | 1 | 2 | 3 | 4 | 5 |
| Vitamin C | | | | | | | | | | | |
| initial | 141 | 142 | 141 | 139 | 140 | 138 | 144 | 141 | 144 | 142 | 143 |
| 1 yr | 105 | 130 | 130 | 127 | 129 | 132 | 107 | 127 | 82 | 113 | 128 |

TABLE 8-continued

Stabilities of vitamin C and calcium pantothenate in soft chewable tablets (%)

| | Examples | | | | | | Comparative Examples | | | | |
|---|---|---|---|---|---|---|---|---|---|---|---|
| | 1 | 2 | 3 | 4 | 5 | 6 | 1 | 2 | 3 | 4 | 5 |
| 2 yr Calcium pantothenate | 86 | 122 | 117 | 119 | 122 | 121 | 85 | 120 | 46 | 91 | 115 |
| initial | 143 | 140 | 141 | 139 | 142 | — | 143 | 141 | — | 143 | 140 |
| 1 yr | 131 | 129 | 130 | 124 | 130 | — | 94 | 61 | — | 103 | 91 |
| 2 yr | 121 | 122 | 122 | 117 | 124 | — | 47 | 24 | — | 54 | 30 |

As clearly illustrated and demonstrated as aboves, the present invention provides an improved soft chewable multivitamin tablet in which vitamin C is separated from calcium pantothenate and/or minerals such as iron, copper, zinc and mixtures thereof in a core or multilaminate form and a process for preparing the same. The soft chewable multivitamin tablet of the present invention maintains its stability over a long-storage time in terms of the content and potency of vitamins while overcoming the problems of incompatibility, bad mouthfeel and palatability.

Although the preferred embodiments of the present invention have been disclosed for illustrative purpose, those who are skilled in the art will appreciate that various modifications, additions and substitutions are possible, without departing from the spirit or scope of the invention as it is set forth herein.

What is claimed is:

1. A process for preparing a soft chewable multivitamin tablet which comprises the steps of:
   (i) dissolving and concentrating sugars in a concentrating tank at a temperature of 120 to 135° C., cooling the concentrated sugars to a temperature of 80 to 100° C., adding a molten mixture of fatty materials and emulsifiers, kneading to a temperature of 60 to 80° C., adding and thoroughly kneading active ingredients comprising vitamin C and not calcium pantothenate, iron, cooper, zinc, or mixtures thereof, and cooling to obtain a kneaded mixture for forming a first layer;
   (ii) dissolving active ingredients comprising calcium pantothenate, iron, cooper, zinc, or mixtures thereof and not vitamin C, with sugars and a stabilizer at a temperature of 40 to 60° C. to obtain a dispersed material for forming a second layer; and,
   (iii) extruding the kneaded mixture and the dispersed material from an extruder having two inlets, rope sizing, and tabletting the extruded kneaded mixture and dispersed material to give a soft chewable multivitamin tablet comprising a first layer and a second layer.

2. The process for preparing a soft chewable multivitamin tablet of claim 1, wherein the soft chewable multivitamin tablet is a tablet having a core.

3. The process for preparing a soft chewable multivitamin tablet of claim 1, wherein the soft chewable multivitamin tablet is a tablet is a multilaminate tablet.

* * * * *